United States Patent [19]

Tamura et al.

[11] Patent Number: 4,956,479

[45] Date of Patent: Sep. 11, 1990

[54] 23-DEOXY-27-CHLORO DERIVATIVES OF LL-F28249 COMPOUNDS

[75] Inventors: Susan Y. Tamura, Hamilton Sq.; Goro Asato, Titusville, both of N.J.

[73] Assignee: American Cyanamid Company, Stamford, Conn.

[21] Appl. No.: 22,848

[22] Filed: Mar. 6, 1987

[51] Int. Cl.$^5$ ................ A61K 31/335; C07D 313/06
[52] U.S. Cl. .................................................. 549/264
[58] Field of Search .......................... 549/264; 514/450

[56] References Cited

U.S. PATENT DOCUMENTS

Re. 32,034 11/1985 Chabala et al. ................. 549/264
4,584,314  4/1986 Burckhardt ..................... 549/264
4,696,922  9/1987 Sturm et al. ..................... 549/264

FOREIGN PATENT DOCUMENTS 170006 2/1986 European Pat. Off. .
2166436A 5/1986 United Kingdom .
2176182 12/1986 United Kingdom ............... 549/264

*Primary Examiner*—Glennon H. Hollrah
*Assistant Examiner*—Ba Trinh
*Attorney, Agent, or Firm*—Estelle J. Tsevdos

[57] ABSTRACT

The present invention relates to novel derivatives of LL-F28249 compounds. These LL-F28249 compounds preferably are derived via a controlled microbiological fermentation of *Streptomyces cyaneogriseus* subspecies *noncyanogenus* having deposit accession number NRRL 15773. The 23-deoxy-27-halo(chloro) derivatives have the 23-hydroxy group of the LL-F28249 compounds replaced by hydrogen and a halogen such as chlorine in the 27-position with the double bond shifted to the 26,26'-position. The novel derivatives of the present invention possess activity as anthelmintic, ectoparasitic, insecticidal, acaricidal and nematicidal agents and are useful in areas of human and animal health and in agricultural crops. Compositions containing the present compounds also are presented herein.

19 Claims, No Drawings

23-DEOXY-27-CHLORO DERIVATIVES OF LL-F28249 COMPOUNDS

BACKGROUND OF THE INVENTION

The present invention relates to new derivatives of the antibiotics collectively defined as LL-F28249. These antibiotics preferably are produced by the fermentation of the microorganism *Streptomyces cyaneogriseus* subspecies *noncyanogenus*, deposited in NRRL under deposit accession number 15773. The LL-F28249 compounds and the method for their production are disclosed in European Patent Application Publication No. 170,006, incorporated herein by reference.

The present invention further relates to methods and compositions for preventing, treating or controlling helminths, ectoparasites, insects, acarids and nematodes infections or infestations in warm-blooded animals and agricultural crops by administering thereto prophylactically, therapeutically or pharmaceutically effective amounts of the present 23-deoxy-LL-F28249 agents (compounds), mixtures thereof or the pharmaceutically and pharmacologically-acceptable salts thereof.

These infections not only cause devastating effects to animals but also seriously effect the economics of farmers in raising meat-producing animals such as swine, sheep, cattle, goats, rabbits and poultry. Further, such infections are a source of great concern for companion animals such as horses, dogs and cats. Therefore, effective methods for the treatment and prevention of these diseases constantly are being sought.

SUMMARY OF THE INVENTION

The present invention provides novel 23-deoxy-27-halo(chloro or bromo) derivatives of the compounds designated LL-F28249 and represented by the following structural formula.

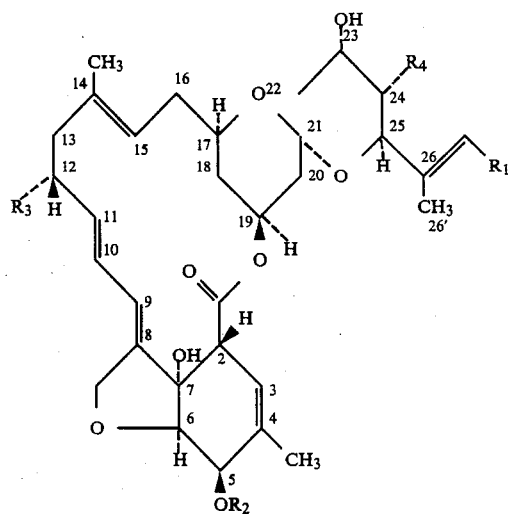

| Component | $R_1$ | $R_2$ | $R_3$ | $R_4$ |
|---|---|---|---|---|
| LL-F28249α | $CH(CH_3)_2$ | H | $CH_3$ | $CH_3$ |
| LL-F28249β | $CH_3$ | H | $CH_3$ | $CH_3$ |
| LL-F28349γ | $CH_3$ | $CH_3$ | $CH_3$ | $CH_3$ |
| LL-F28249ε | $CH(CH_3)_2$ | H | H | $CH_3$ |
| LL-F28249δ | $CH_2CH_3$ | H | $CH_3$ | $CH_3$ |
| LL-F28249θ | $CH(CH_3)_2$ | H | $CH_3$ | $CH_2CH_3$ |
| LL-F28249ι | $CH(CH_3)_2$ | H | $CH_2CH_3$ | $CH_3$ |
| LL-F28249λ | $CH(CH_3)_2$ | $CH_3$ | $CH_3$ | $CH_3$ |

The compounds of the present invention are represented by structural formula (I),

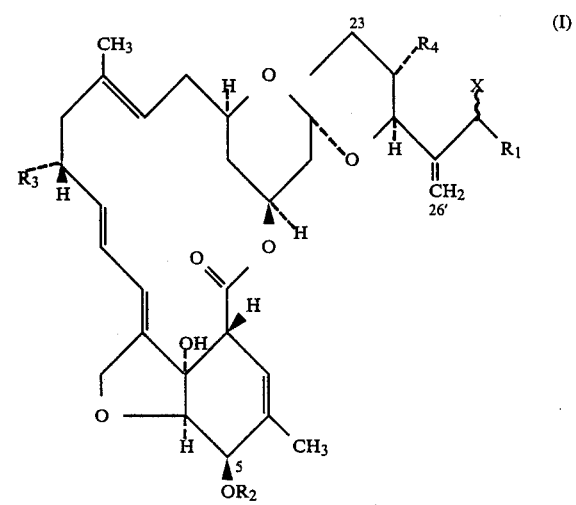

wherein $R_1$ is methyl, ethyl or isopropyl; $R_2$ is hydrogen or methyl; $R_3$ is hydrogen, methyl or ethyl; $R_4$ is methyl or ethyl; and X is halogen, such as chlorine or bromine.

The compounds of the present invention are useful anthelmintics, ectoparasiticides, insecticides, acaricides and nematicides in treating, preventing or controlling such diseases in warm-blooded animals, such as poultry, cattle, sheep, swine, rabbits, horses, dogs, cats and human beings and in agricultural crops.

Although these diseases have been recognized for years and therapies exist for treatment and prevention of the diseases, the present invention provides novel compounds in the search for effective such therapy. For instance, U.S. patent application Ser. Nos. 907,283, 907,188, 907,281, 907,259, 907,187 and 907,284 of Asato and Asato et al, filed on Sept. 12, 1986 and incorporated herein by reference thereto, provide novel compounds for such uses. Also U.S. patent application Ser. Nos. 022849, 022850, 022906, 022846 and 022847 of Asato et al, filed concurrently herewith and incorporated herein by reference thereto provide compounds for such treatments.

U.S. Pat. No. 3,950,360, Aoki et al, Apr. 13, 1976, discloses certain antibiotic substances obtained by culturing a Streptomyces microorganism, said compounds being useful as insecticides and acaricides. Further, an entire series of U.S. patents relates to certain compounds produced by the fermentation of *Streptomyces avermitilis* (U.S. Pat. No. 4,171,314, Chabala et al, Oct. 16, 1979; U.S. Pat. No. 4,199,569, Chabala et al, Apr. 22, 1980; U.S. Pat. No. 4,206,205, Mrozik et al, June 3, 1980; U.S. Pat. No. 4,310,519, Albers-Schonberg, Jan. 12, 1982; U.S. Pat. No. 4,333,925, Buhs et al, June 8, 1982). U.S. Pat. No. 4,423,209, Mrozik, Dec. 27, 1983 relates to the process of converting some of these less desirable components to more preferred ones. British Patent Application No. 2166436A of Ward et al relates to antibiotics also, as does Belgium Application No. 904,709A.

The present compounds or the pharmaceutically and pharmacologically-acceptable salts thereof exhibit excellent and effective treatment, prevention and/or control of these serious diseases of warm-blooded animals.

It is an object of the present invention, therefore, to provide novel 23-deoxy-27-halo compounds of the LL-F28249 compounds. It is another object to provide novel 23-deoxy-27-chloro or bromo such compounds.

It is a further object of the present invention to provide novel methods for the treatment, prevention or control of helminth, ectoparasite, insect, acarid and nematode infections and infestations in warm-blooded animals and agricultural crops.

It also is an object of the present invention to provide novel compositions to effectively control, prevent or treat said diseases in warm-blooded animals.

These and further objects will become apparent by the below-provided detailed description of the invention.

DETAILED DESCRIPTION OF THE INVENTION

The compounds of the invention are represented by structural formula (I),

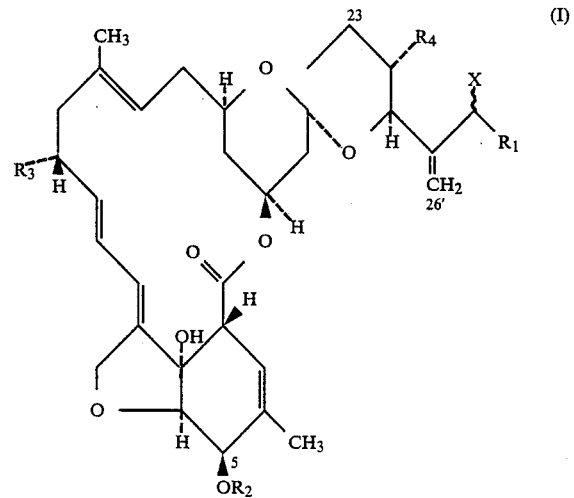

wherein $R_1$ is methyl, ethyl or isopropyl; $R_2$ is hydrogen or methyl; $R_3$ is hydrogen, methyl or ethyl; $R_4$ is methyl or ethyl; and X is halogen, such as chlorine or bromine.

Preferably, $R_1$ is isopropyl; $R_2$ is hydrogen or methyl; $R_3$ is methyl; $R_4$ is methyl and X; is chlorine or bromine. The most preferred compounds include those in which $R_1$ is isopropyl; $R_2$ is hydrogen; $R_3$ is methyl; $R_4$ is methyl; and X is chlorine or bromine.

The 23-deoxy derivatives of LL-F28249 are prepared by converting the 23-hydroxyl group to a 23-halo group. The halo compound is then reduced with a reducing agent such as tributyltin hydride in the presence of a free radical initiator such as azobisisobutyronitrile (AIBN) to afford the 23-deoxy-LL-F28249 compound.

A preferred 23-halo compound is 23-bromo-LL-F28249 compound which is readily prepared by reacting the appropriate LL-F28249 compound with about 1.0 to 1.5 molar equivalents of triphenylphosphine dibromide, preferably 1.0 to 1.25 molar equivalents, in an inert solvent such as acetonitrile, carbon tetrachloride, dimethylformamide or benzonitrile under $N_2$ atmosphere at $-20°$ C. to $25°$ C., preferably $0°$ C. to $25°$ C. The reaction occurs selectively at the 23 position. The bromide is then reduced with a reducing agent such as tributyltin hydride in the presence of a free radical initiator such as azobisisobutyronitrile in an inert solvent such as toluene or xylene at reflux temperature to give the 23-deoxy-LL-F28249 compound.

The 23-deoxy-LL-F28249 compound is then reacted with N-chlorosuccinimide (NCS) in methanol at $0°$ C. to $35°$ C. to afford a 23-deoxy-27-chloro-LL-F28249 compound with the side-chain double bond at the 26,26'-position. The 23-deoxy-27-bromo-LL-F28249 compound with the double bond at the 26,26'-position is obtained by reacting the 23-deoxy-LL-F28249 compound with N-bromoacetamide (NBA) in aqueous acetone at $-10°$ C. to $10°$ C. These transformations are schematically illustrated as follows:

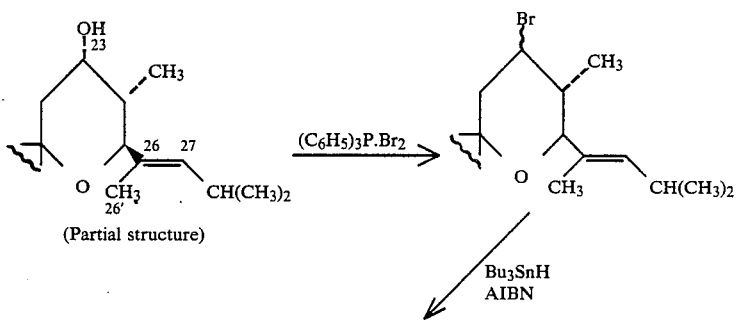

(Partial structure)

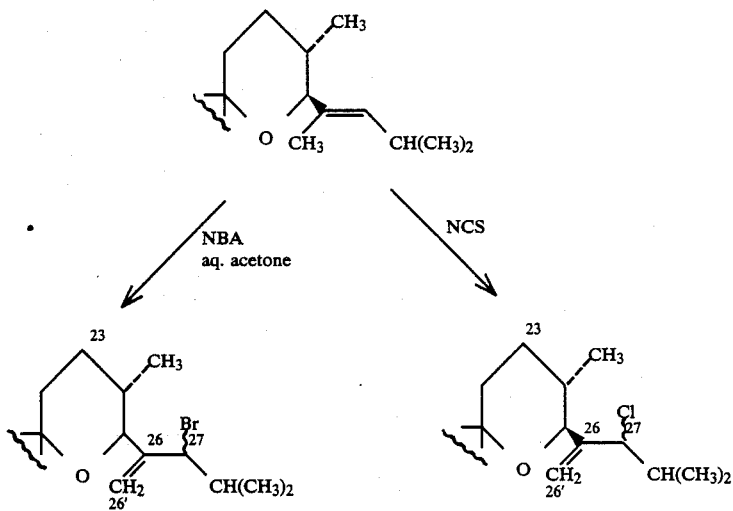

These novel derivatives are purified by conventional chromatographic techniques, such as flash-column chromatography, high-performance liquid chromatography (HPLC) or preparative-plate chromatography using silica gel.

The compounds of the present invention are useful as anthelmintics, ectoparasiticides, insecticides, acaricides and nematicides.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum primarily attack the intestinal tract, while others, such as Haemonchus and Ostertagia, are most prevalent in the stomach. Still others, such as Dictyocaulus, are found in the lungs. However, other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs, and, if left untreated, may result in death of the infected host. The LL-F28249 compound derivatives of the present invention unexpectedly have high activity against these parasites. Additionally, the compounds of this invention also are active against Dirofilaria in dogs, Nematospiroides, Syphacia, Aspiculuris in rodents, arthropod ectoparasites such as ticks, mites, lice, fleas, blowfly, of animals and birds, the ectoparasite Lucilia sp. of sheep, biting insects and migrating dipterous larvae such as Hypoderma sp. in cattle, Gastrophilus in horses and Cuterebra sp. in rodents.

The compounds of the present invention also are useful in treating, preventing or controlling parasites (collectively includes ecto and/or endoparasites) which infect human beings, as well. The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The present compounds also are of value against arthropods parasitizing man, biting insects and other dipterous pests causing annoyance to man.

These compounds further are active against household pests such as the cockroach, Blattella sp., clothes moth, Tineola sp., carpet beetle Attagenus sp. and the housefly Musca domestica.

Insect pests of stored grains such as Tribolium sp., Tenebrio sp., and of agricultural plants such as spider mites (Tetranychus sp.), aphids (Acyrthiosiphon sp.), southern army worms, tobacco budworms, boll weevils migratory orthopterans, such as locusts and immature stages of insects living on plant tissue are controlled by the present compounds, as well as the control of soil nematodes and plant parasites such as Meloidogyne sp.

The compounds of the present invention may be administered orally or parenterally for animal and human usage, while they may be formulated in liquid or solid form for agricultural use. Oral administration may take the form of a unit dosage form such as a capsule, bolus or tablet, or as a liquid drench where used as an anthelmintic for animals.

The animal drench is normally a solution, suspension or dispersion of the active compound, usually in water, together with a suspending agent such as bentonite and a wetting agent or like excipient. Generally, the drenches also contain an antifoaming agent. Drench formulations generally contain about 0.001% to 0.5%, by weight, of the active compound. Preferred drench formulations contain about 0.01% to 0.1% by weight. Capsules and boluses comprise the active compound admixed with a carrier vehicle such as starch, talc, magnesium stearate or di-calcium phosphate.

Where it is desired to administer the 23-deoxy-27-halo(chloro or bromo)-LL-F28249 derivatives in a dry, solid unit dosage form, capsules, boluses or tablets containing the desired amount of active compound usually are employed. These dosage forms are prepared by intimately and uniformly mixing the active compound with suitable finely divided diluents, fillers, disintegrating agents and/or binders such as starch, lactose, talc, magnesium stearate, vegetable gums and the like. Such unit dosage formulations may be varied widely with respect to their total weight and content of the active compound depending upon factors such as the type of host animals to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the active compounds of the invention may be administered to animals parenterally such as by intraruminal, intramuscular, intratracheal or subcutaneous injection. In such as event, the active compound is dissolved or dispersed in a liquid carrier vehicle.

For parenteral administration, the active compound is suitably admixed with an acceptable vehicle, preferably a vegetable oil such as peanut oil, cotton seed oil or the like. Other parenteral vehicle such as organic preparations using solketal, glycerol formal and aqueous parenteral formulation also are used. The active LL-F28249 compound derivative or derivatives are dissolved or suspended in the parenteral formulation for administration. Such formulations generally contain about 0.005% to 5%, by weight, of the active compound.

Although the compounds of the present invention are primarily used in the treatment, prevention or control of helminthiasis, they also are useful in the prevention, treatment or control of diseases caused by other parasites (collectively both ecto- and/or endoparasites). For example, arthropod parasites such as ticks, lice, fleas, mites and other biting insects in domesticated animals and poultry are controlled by the present compounds. These compounds also are effective in treatment of parasitic diseases which occur in other animals including human beings. The optimum amount to be employed will, of course, depend upon the particular compound employed, the species of animal to be treated and the type and severity of parasitic infection or infestation. Generally, the amount useful in oral administration of these novel compounds is about 0.001 mg per kg to 10 mg per kg of animal body weight, such total dose being given at one time or in divided doses over a relatively short period of time (1-5 days). The preferred compounds of the invention give excellent control of such parasites in animals by administering about 0.025 mg per kg to 3 mg per kg of animal body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of animals' feed or dissolved or suspended in the drinking water, compositions are provided in which the active compound or compounds are intimately dispersed in an inert carrier or diluent. An inert carrier is one that will not react with the active component and that will be administered safely to animals. Preferably, a carrier for feed administration is one that is, or may be, an ingredient of the animal ration.

Suitable compositions include feed premixes or supplements in which the active compound is present in relatively large amounts, wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing about 0.005% to 2.0%, by weight of the active compound are particularly suitable as feed premixes. Feed supplements, which are fed directly to the animal, contain about 0.0002% to 0.3%, by weight, of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular derivative employed, the compounds of this invention are usually fed at concentrations of about 0.00001% to 0.02% in the feed in order to achieve the desired antiparasitic result.

The compounds also may be administered by pouring on the skin of animals via a solution. Generally, the active compounds are dissolved in suitable inert solvents, such as dimethylsulfoxide, propylene glycol or the like, alternatively in combination of solvents, for the pour-on administration.

The compounds of this invention also are useful in combating agricultural pests that inflict damage upon growing or stored crops. The present compounds are applied, using known techniques such as sprays, dusts, emulsions and the like, to the growing or stored crops to effect protection from agricultural pests.

The present invention is illustrated by the following examples which are illustrative of said invention and not limitative thereof.

EXAMPLE 1

23-Bromo-LL-F28249α

In 10 mL of dry acetonitrile, 0.161 g of triphenylphosphine and 28 μL of bromine are dissolved, and this solution is added dropwise under $N_2$ atmosphere and 262.2 mg of LL-F28249α in 5 mL of dry acetonitrile cooled in an ice bath. After stirring for 45 minutes in the ice bath, the reaction mixture is stirred at room temperature for 19 hours. The reaction is quenched with 10 drops of water. The mixture is evaporated to dryness, and the residue is chromatographed on silica gel using 0.75−1.0% i-PrOH in $CH_2Cl_2$. After stripping of solvents, this yields 75.7 mg of the title compound that is identified by mass spectrometry and NMR spectroscopy.

EXAMPLE 2

23-Deoxy-LL-F28249α

In 2 mL of toluene, 35.9 mg of 23-bromo-LL-F28249α, a catalytic amount of azobisisobutyronitrile (AIBN) and 17 μL of tributyltin hydride under $N_2$ atmosphere are heated at reflux temperature for 0.5 hours. The mixture is evaporated to dryness, and the residue is chromatographed on silica gel using initially $CH_2Cl_2$ and then 1% i-PrOH in $CH_2Cl_2$ as eluents. The fractions from the latter solvent mixture contain the product with traces of tin compounds. Partitioning between acetonitrile and hexane affords separation of the desired product in the acetonitrile layer. Further extraction of the hexane layer with acetonitrile affords additional product. The combined acetonitrile layers are evaporated to dryness. The product is characterized by mass spectrometry and NMR spectroscopy.

EXAMPLES 3 AND 4

23-Bromo-LL-F28249γ

Following the procedures of Example 1, LL-F28249γ is converted into the title compound and identified by mass spectrometry and NMR spectroscopy.

Similarly, LL-F28249γ is converted to 23-bromo-LL-F28249γ.

EXAMPLES 5 AND 6

23 -Deoxy-LL-F28249γ

Using the procedure of Example 2, 23-bromo-LL-F28249 γ is reduced with tributyltin hydride to give the title compound that is identified by mass spectrometry and NMR spectroscopy.

Similarly, 23-bromo-LL-F28249γ is reduced to afford 23-deoxy-LL-F28249γ.

EXAMPLES 7–13

Using the procedures described in Example 1 and 2, the following 23-deoxy-LL-F28249 compounds are prepared:

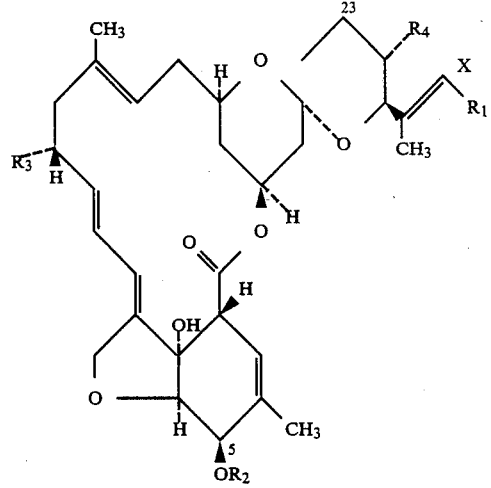

| $R_1$ | $R_2$ | $R_3$ | $R_4$ |
|---|---|---|---|
| $CH(CH_3)_2$ | H | $CH_3$ | $CH_3$ |
| $CH_3$ | H | $CH_3$ | $CH_3$ |
| $CH(CH_3)_2$ | H | H | $CH_3$ |
| $CH_2CH_3$ | H | $CH_3$ | $CH_3$ |
| $CH(CH_3)_2$ | H | $CH_3$ | $CH_2CH_3$ |
| $CH(CH_3)_2$ | H | $CH_2CH_3$ | $CH_3$ |

-continued

| $R_1$ | $R_2$ | $R_3$ | $R_4$ |
|---|---|---|---|
| $CH(CH_3)_2$ | $CH_3$ | $CH_3$ | $CH_3$ |

EXAMPLE 14

27 -Bromo-26-Methylene-LL-F28249α

In 2.5 mL of 80% aqueous acetone, 100 mg of 23-deoxy-LL-F28249α is stirred at 0° C. under $N_2$, and 30 mg of N-bromoacetamide in 3 mL of acetone is added dropwise. After stirring for 2 hours at 0° C., the solution is diluted with 25 mL of $Et_2O$ and then washed with 4 mL of brine. The ethereal layer is dried over $MgSO_4$ and evaporated to dryness. The residue is chromatographed on $SiO_2$ using 1.5% i-PrOH/$CH_2Cl_2$ as eluent on a flash-chromatography column. The fractions are collected and evaporated to dryness to afford 57 mg of the title compound that is identified by mass spectrometry and nuclear magnetic resonance (NMR) spectroscopy.

EXAMPLES 15–18

Using the procedure of Example 14, the following 27-bromo compounds are prepared using the compounds prepared in Examples 7–13:

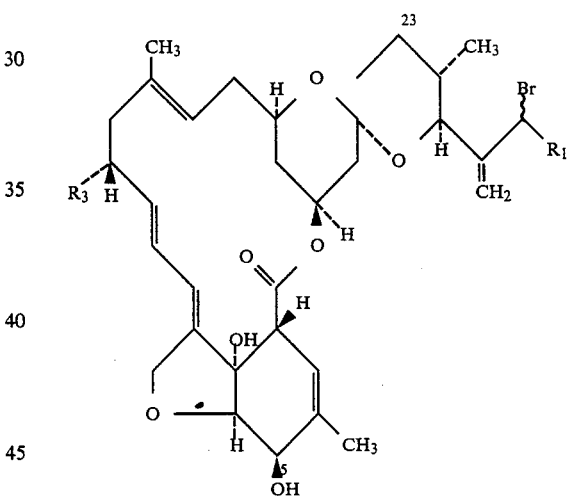

| $R_1$ | $R_2$ | $R_3$ |
|---|---|---|
| $CH(CH_3)_2$ | H | $CH_2CH_3$ |
| $CH_3$ | H | $CH_3$ |
| $CH(CH_3)_2$ | H | H |
| $CH_2CH_3$ | H | $CH_3$ |

EXAMPLE 19

27-Chloro-26-Methylene-LL-F28249α

In 1 mL of methanol, 32 mg N-chloro-succinimide is stirred at 0° C. under $N_2$ atmosphere, and 130 mg of LL-F-b 28249α in 2 mL of methanol is added dropwise. The solution is allowed to warm to room temperature and stirred for 19 hours. The reaction misture is diluted with 30 mL of $ET_2O$ and washed successively with 5 mL of saturated $NaHCO_3$ followed by 5 mL of brine. The ethereal layer is dried ($MgSO_4$) and evaporated. The residue is purified by flash-chromatography on silica gel using 1½%–2% i-PrOH/$CH_2Cl_2$ as eluent. The solvent is removed in vacuo from the purest fractions to afford 92.7 mg of the title compound that is identified by mass spectrometry and nuclear magnetic resonance (NMR) spectroscopy.

EXAMPLES 20-24

Using the procedure of Example 19, the following 27-chloro compounds are prepared using the compounds prepared in Examples 7-13:

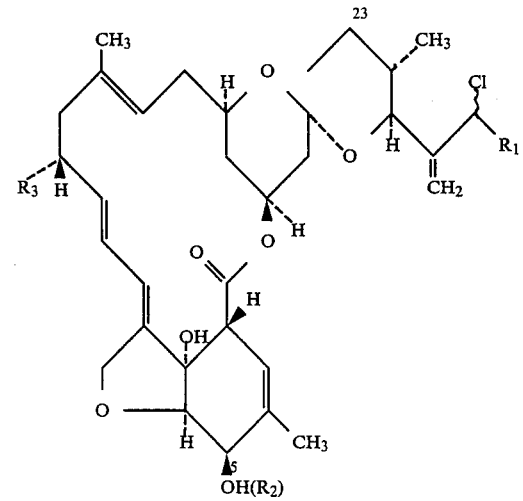

| $R_1$ | $R_3$ | $(R_2)$ |
|---|---|---|
| $CH(CH_3)_2$ | $CH_2CH_3$ | |
| $CH_3$ | $CH_3$ | |
| $CH(CH_3)_2$ | $H$ | |
| $CH_2CH_3$ | $CH_3$ | |
| $CH(CH_3)_2$ | $CH_3$ | $CH_3$ |

What is claimed is:

1. A compound represented by formula (I),

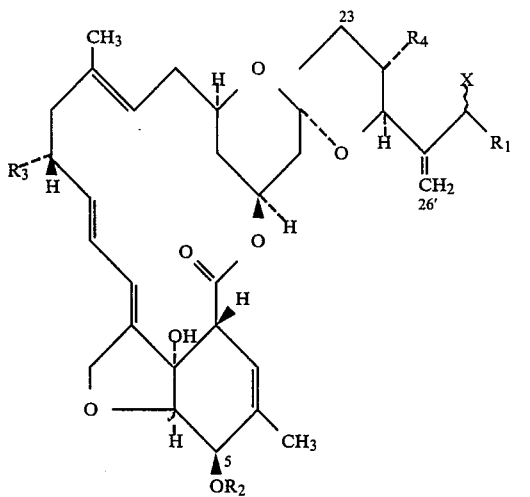

wherein $R_1$ is methyl, ethyl or isopropyl; $R_2$ is hydrogen or methyl; $R_3$ is hydrogen, methyl or ethyl; $R_4$ is methyl or ethyl; and X is chlorine.

2. A compound according to claim 1, wherein $R_1$ is isopropyl; $R_2$ is hydrogen or methyl; $R_3$ is methyl; $R_4$ is methyl; and X is chlorine.

3. A compound according to claim 2, wherein $R_1$ is isopropyl; $R_2$ is hydrogen; $R_3$ is methyl; $R_4$ is methyl; and X is chlorine.

4. A method for the prevention, treatment or control of parasitic infections in warm-blooded animals, said method comprising: orally, topically or parenterally administering to an animal infected with parasites, a parasiticidally-effective amount of a compound represented by structural formula (I),

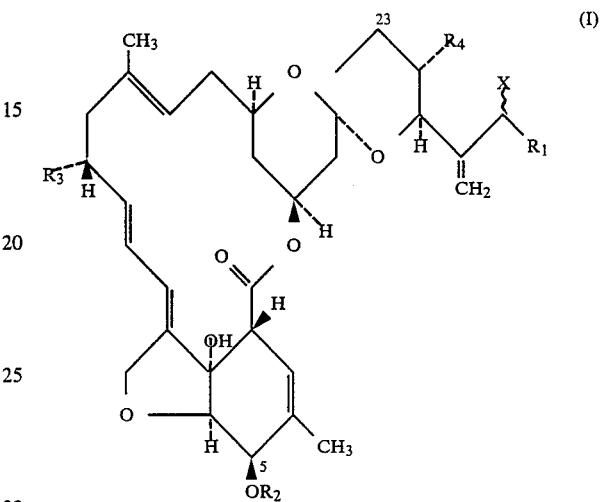

wherein $R_1$ is methyl, ethyl or isopropyl; $R_2$ is hydrogen or methyl; $R_3$ is hydrogen, methyl or ethyl; $R_4$ is methyl or ethyl; and X is chlorine.

5. A method according to claim 4, wherein said compound has $R_1$ as isopropyl; $R_2$ is hydrogen or methyl; $R_3$ is methyl; $R_4$ is methyl; and X is chlorine.

6. A method according to claim 5, wherein said compound has $R_1$ as isopropyl; $R_2$ is hydrogen; $R_3$ is methyl; $R_4$ is methyl; and X is chlorine.

7. A method for protecting crops, trees, shrubs, stored grain and ornamentals from attack by insects or acarids, said method comprising: applying to said crops, trees, shrubs, stored grains and ornamentals or locus in which they are stored or growing an insecticidally or acaricidally effective amount of the compound represented by structural formula (I), wherein $R_1$ is methyl, ethyl or isopropyl; $R_2$ is hydrogen or methyl; $R_3$ is hydrogen, methyl or ethyl; $R_4$ is methyl or ethyl; and X is chlorine.

8. A method according to claim 7, wherein said compound is applied to the foliage of crops and plants, the soil in which they are grown or the trunk thereof.

9. A method according to claim 8, wherein said compound has $R_1$ as isopropyl; $R_2$ is hydrogen or methyl; $R_3$ is methyl; $R_4$ is methyl; and X is chlorine.

10. A method according to claim 9, wherein said compound has $R_1$ as isopropyl; $R_2$ is hydrogen; $R_3$ is methyl; $R_4$ is methyl; and X is chlorine.

11. A method for the control of plant nematodes, said method comprising: applying to the foliage of plants, the soil in which they are grown or into the trunks thereof, a nematocidally-effective amount of the compound represented by structural formula (I),

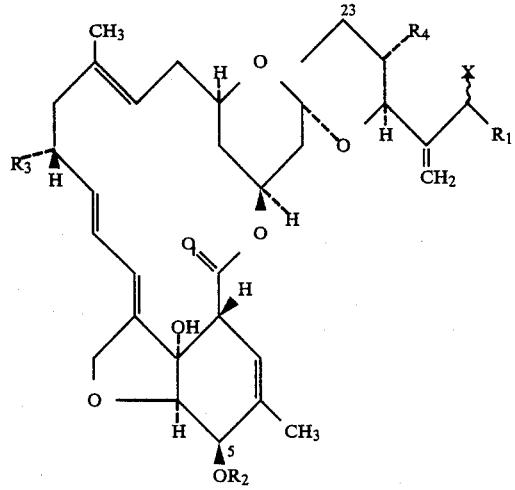

wherein $R_1$ is methyl, ethyl or isopropyl; $R_2$ is hydrogen or methyl; $R_3$ is hydrogen, methyl or ethyl; $R_4$ is methyl or ethyl; and X is chlorine.

12. A method according to claim 11, wherein said compound has $R_1$ as isopropyl; $R_2$ is hydrogen or methyl; $R_3$ is methyl; $R_4$ is methyl; and X is chlorine.

13. A method according to claim 12, wherein said compound has $R_1$ as isopropyl; $R_2$ is hydrogen; $R_3$ is methyl; $R_4$ is methyl; and X is chlorine.

14. A composition comprising: a pharmacologically effective amount of the compound represented by structural formula (I),

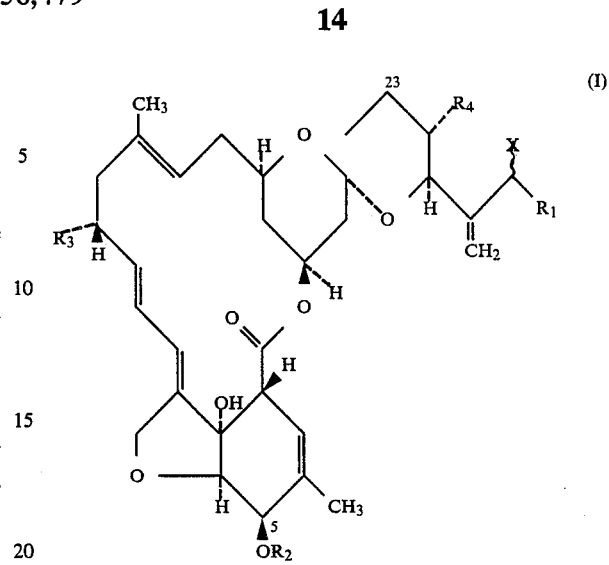

wherein $R_1$ is methyl, ethyl or isopropyl; $R_2$ is hydrogen or methyl; $R_3$ is hydrogen, methyl or ethyl; $R_4$ is methyl or ethyl; X is chlorine; wherein said composition is used to control endo- and ectoparasitic infections which infect warm-blooded animals.

15. A composition according to claim 14, wherein said compound has $R_1$ as isopropyl; $R_2$ is hydrogen or methyl; $R_3$ is methyl; $R_4$ is methyl; and X is chlorine.

16. A composition according to claim 15, wherein said compound has $R_1$ as isopropyl; $R_2$ is hydrogen; $R_3$ is methyl; $R_4$ is methyl; and X is chlorine.

17. A composition comprising: an insecticidally-effective amount of the compound represented by structural formula (I),

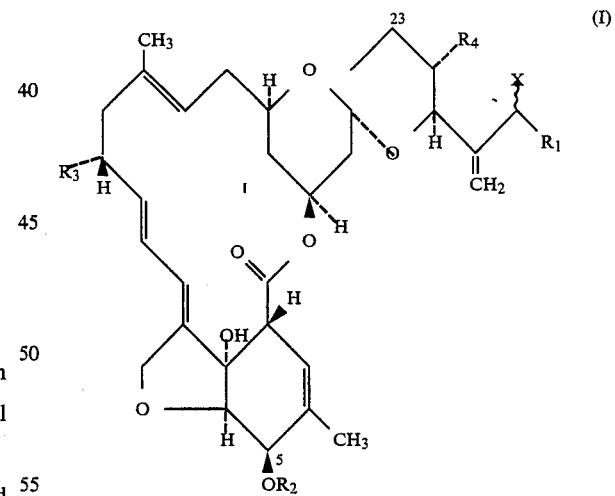

wherein $R_1$ is methyl, ethyl or isopropyl; $R_2$ is hydrogen or methyl; $R_3$ is hydrogen, methyl or ethyl; $R_4$ is methyl or ethyl; X is chlorine; and an inert carrier; wherein said composition is used to control plants infected with insects or acarids.

18. A composition according to claim 17, wherein said compound has $R_1$ as isopropyl; $R_2$ is hydrogen or methyl; $R_3$ is methyl; $R_4$ is methyl; and X is chlorine.

19. A composition according to claim 18, wherein said compound has $R_1$ as isopropyl; $R_2$ is hydrogen; $R_3$ is methyl; $R_4$ is methyl; and X is chlorine.

* * * * *